US008968651B2

(12) United States Patent
Hayashi et al.

(10) Patent No.: US 8,968,651 B2
(45) Date of Patent: Mar. 3, 2015

(54) STERILIZATION METHOD

(75) Inventors: Hirofumi Hayashi, Wakayama (JP);
Tomoyuki Hirose, Wakayama (JP);
Kazuhiro Kimura, Wakayama (JP);
Masaaki Mike, Wakayama (JP);
Ryuichi Iwasaki, Wakayama (JP);
Shigeru Masuda, Wakayama (JP); Toru Tanibata, Santa Clara, CA (US);
Joongsoo Kim, Los Altos, CA (US);
Sang Hun Lee, San Ramon, CA (US);
Jae-Mo Koo, Palo Alto, CA (US); Orion Weihe, Fremont, CA (US); Andrew Way, San Jose, CA (US)

(73) Assignee: Noxilizer, Inc., Baltimore, MD (US)

( * ) Notice: Subject to any disclaimer, the term of this patent is extended or adjusted under 35 U.S.C. 154(b) by 189 days.

(21) Appl. No.: 13/145,744

(22) PCT Filed: Mar. 10, 2010

(86) PCT No.: PCT/US2010/026824
§ 371 (c)(1),
(2), (4) Date: Jul. 21, 2011

(87) PCT Pub. No.: WO2010/104948
PCT Pub. Date: Sep. 16, 2010

(65) Prior Publication Data
US 2011/0274583 A1 Nov. 10, 2011

(30) Foreign Application Priority Data

Mar. 12, 2009 (JP) .................................. 2009-059408

(51) Int. Cl.
*A61L 2/14* (2006.01)
*A61L 2/20* (2006.01)

(52) U.S. Cl.
CPC . *A61L 2/14* (2013.01); *A61L 2/202* (2013.01);
*A61L 2202/122* (2013.01); *A61L 2202/13* (2013.01); *A61L 2202/14* (2013.01); *A61L 2202/24* (2013.01)
USPC .......................................................... 422/29

(58) Field of Classification Search
USPC ...................................................... 422/28–29
See application file for complete search history.

(56) References Cited

U.S. PATENT DOCUMENTS

| 5,186,893 A | 2/1993 | Moulton et al. |
| 2004/0037736 A1 | 2/2004 | Perruchot et al. |
| 2007/0292305 A1 | 12/2007 | Dempsey et al. |
| 2008/0317626 A1 | 12/2008 | Arnold et al. |
| 2011/0085938 A1* | 4/2011 | Carbone et al. ................. 422/29 |

FOREIGN PATENT DOCUMENTS

| EP | 10751353.3-1356 | 8/2013 |
| JP | 58162276 A | 9/1983 |

(Continued)

OTHER PUBLICATIONS

Iwanami Dictionary of Physics and Chemistry, 4th Edition, Japan, Iwanami Shoten, Publishers, 1987, p. 498 (English translation).

*Primary Examiner* — Sean E Conley
*Assistant Examiner* — Donald Spamer
(74) *Attorney, Agent, or Firm* — Rahman LLC

(57) ABSTRACT

By focusing on the fact that nitrogen dioxide exhibits an increased sterilizing effect among other sterilant gases including nitrogen oxide, the present invention is made to provide a sterilization method which may be suitably used for sterilizing items to be sterilized such as medical instruments which require increased reliability by using a high concentration $NO_2$ gas of 5,000 ppm or above, for example. An inside of a sterilizing chamber containing an item to be sterilized is humidified, and a concentration of $NO_2$ in the sterilizing chamber is made to be from 9 to 100 mg/L by filling a high concentration $NO_2$ gas.

8 Claims, 7 Drawing Sheets

(56) References Cited

FOREIGN PATENT DOCUMENTS

| | | |
|---|---|---|
| JP | 04020345 A | 1/1992 |
| JP | 2009542333 A | 12/2009 |
| WO | WO2008005313 A2 | 1/2008 |
| WO | 2010051378 A1 | 5/2010 |
| WO | 2010102000 A2 | 9/2010 |
| WO | 2011002700 A2 | 1/2011 |

\* cited by examiner

STERILIZATION METHOD

TECHNICAL FIELD

The present invention relates to a sterilization method. More particularly, the present invention relates to a method for sterilizing an item to be sterilized (in particular, medical instruments) by a high concentration $NO_2$ gas introduced in a sterilizing chamber under a specific relative humidity.

BACKGROUND ART

Conventionally, as sterilizing methods of medical instruments, high-pressure steam sterilization (hereinafter, simply referred to as "AC") and ethylene oxide gas sterilization (hereinafter, simply referred to as "EOG sterilization") have been widely used.

AC is a sterilization method in which an item to be sterilized is exposed under a high temperature at approximately 135° C., and has been widely used for medical instruments made of such as glass materials. However, there is a disadvantage that limitations exist in items to be sterilized since sterilization is performed under a high temperature condition. For example, there is a problem that heat labile materials such as plastics cannot be sterilized by AC.

On the other hand, EOG sterilization can be used for plastics since it can be performed at a lower temperature of 70° C. or below. However, due to its toxicity and risk of explosion, there is a disadvantage that EOG needs to be securely stored so as not to cause a problem associated with hygienics and safety, and sufficient care needs to be taken in handling. In addition, when EOG is supplied from a tank (cylinder) to a sterilizing apparatus via a pipe, the occurrence of weight reduction needs to be constantly monitored by measuring the weight of the cylinder for the purpose of preventing unexpected leakage from such as the pipes.

Besides those sterilization methods, a sterilization method using hydrogen peroxide (hereinafter, simply referred to as "$H_2O_2$") has been used. Hydrogen peroxide is simple to use and manage as compared with EOG, and is useful from the safety perspective. However, since hydrogen peroxide is used in the form of an aqueous solution, the permeability to detail portions such as an inside of a tube is inferior to the AC or EOG sterilization.

As an alternative method to the AC or EOG sterilization, as shown in Japanese Unexamined Patent Publication No. 240864/1988, a sterilization method using high concentration ozone (hereinafter, simply referred to as "$O_3$") has also been used in which high concentration ozone is generated by providing a circulating pump in a position downstream from the ozone tank and upstream from the ozonizer and circulating ozone therethrough. In the method, an advantage exists that the generation of ozone and the decomposition of ozone after use are simple. However, there are disadvantages that high concentration ozone is explosive and gives the substantial damage to plastics.

As a sterilization method with no risk of explosion as compared with the above-mentioned various sterilization methods, a sterilization method using nitrogen oxide (hereinafter, simply referred to as "NOx") has been proposed. In the method of Japanese Unexamined Patent Publication No. 162276/1983, for example, a gas mixture which is obtained by performing a plasma treatment to the gas mixture of oxygen and nitrogen is used for the purpose of sterilizing *Escherichia coli* present on such as food surface. In the method, a gas mixture of nitrogen oxide and ozone is prepared by performing the plasma treatment to a gas mixture introduced from an oxygen cylinder and nitrogen cylinder. The prepared gas mixture is sprayed on the surface of food to sterilize *Escherichia coli* present on the surface. Since the sterilization process can be performed at a moderate temperature, there are advantages that the method can be used for various items to be sterilized, and that sterilant gas does not need to be stored since nitrogen oxide is generated on demand.

DISCLOSURE OF INVENTION

In the sterilizing apparatus of Japanese Unexamined Patent Publication No. 162276/1983, however, nitrogen oxide is prepared by so called "single pass", a single plasma treatment of a gas mixture of oxygen and nitrogen. In addition, nitrogen oxide is sprayed on the surface of food in an open space and the nitrogen oxide after the treatment is directly released to the atmosphere. As a result, the concentration of sterilant gas including nitrogen oxide is, at most, an order of several ppm and is useful to the extent of sterilizing *Escherichia coli* (and sterilization is performed on *Escherichia coli* present only on the surface of food). Accordingly, there is a problem that the method can never be used for the purpose of a high level of sterilization where increased reliability is desired (for example, medical instruments attached with germs; more specifically, sterilization of a microspace such as between scissors and an inside of a tube).

The present invention is provided in view of the above-mentioned problems. By focusing on the fact that nitrogen dioxide (hereinafter, simply referred to as "$NO_2$") exhibits an increased sterilizing effect among other sterilant gases including nitrogen oxide, an object of the present invention is to provide a sterilization method which may be suitably used for sterilizing items to be sterilized such as medical instruments which require increased reliability by using a high concentration $NO_2$ gas of 5,000 ppm or above, for example.

The sterilization method according to the present invention includes humidifying an inside of a sterilizing chamber containing an item to be sterilized, and filling a high concentration $NO_2$ gas to obtain an $NO_2$ concentration of from 9 to 100 mg/L in the sterilizing chamber.

Preferably, the inside of the chamber is humidified to obtain a relative humidity of from 10 to 90% R.H.

Preferably, a humidifying apparatus for humidifying in the sterilizing chamber is provided, and a high concentration $NO_2$ gas is filled in the sterilizing chamber after humidifying with the humidifying apparatus.

Preferably, the humidifying apparatus is configured to include an evaporation portion communicating with the sterilizing chamber, and a heater for heating the evaporation portion.

Preferably, an exhausting apparatus is provided in the sterilizing chamber, and the humidification is performed or the high concentration $NO_2$ gas is filled in the sterilizing chamber after a pressure of an inside of the sterilizing chamber is decreased to from 0.01 KPa to 1 KPa (absolute pressure).

Preferably, the high concentration $NO_2$ gas is generated by displacing a gas mixture including nitrogen and oxygen into a plasma state with a plasma generator.

Preferably, the high concentration $NO_2$ gas is filled in a plurality of times to gradually increase the number of $NO_2$ molecules and an internal pressure in the sterilizing chamber.

Preferably, a pressure difference between an outside atmospheric pressure and a pressure in the sterilizing chamber at the time of completing the filling of the high concentration $NO_2$ is from −1 KPa to −95 KPa (relative pressure).

Preferably, an ambient temperature inside the sterilizing chamber filled with the high concentration $NO_2$ gas is maintained to from 10 to 90° C.

Preferably, an item to be sterilized having a narrow opening with an internal diameter of from 1 to 4 mm is contained in the sterilizing chamber for between 10 and 480 minutes, and wherein the sterilizing chamber is humidified to reach a relative humidity of from 10 to 90% R.H., and is filled with the high concentration $NO_2$ gas to obtain an $NO_2$ concentration of from 9 to 100 mg/L in the chamber.

Preferably, an item to be sterilized having crossover opposing surfaces is contained in the sterilizing chamber for between 10 and 480 minutes, and wherein the sterilizing chamber is humidified to reach a relative humidity of from 10 to 90% R.H., and is filled with the high concentration $NO_2$ gas to obtain an $NO_2$ concentration of from 9 to 100 mg/L in the chamber.

BEST MODE FOR CARRYING OUT THE INVENTION

Hereinafter, Embodiments of the present invention is described by referring to the Examples illustrated in drawings. The sterilization method of the present Embodiment is characterized in that an inside of a sterilizing chamber 2 containing an item to be sterilized is humidified, and that a high concentration $NO_2$ is filled therein such that the concentration of $NO_2$ in the sterilizing chamber 2 is increased to from 9 to 100 mg/L.

Figure 1:
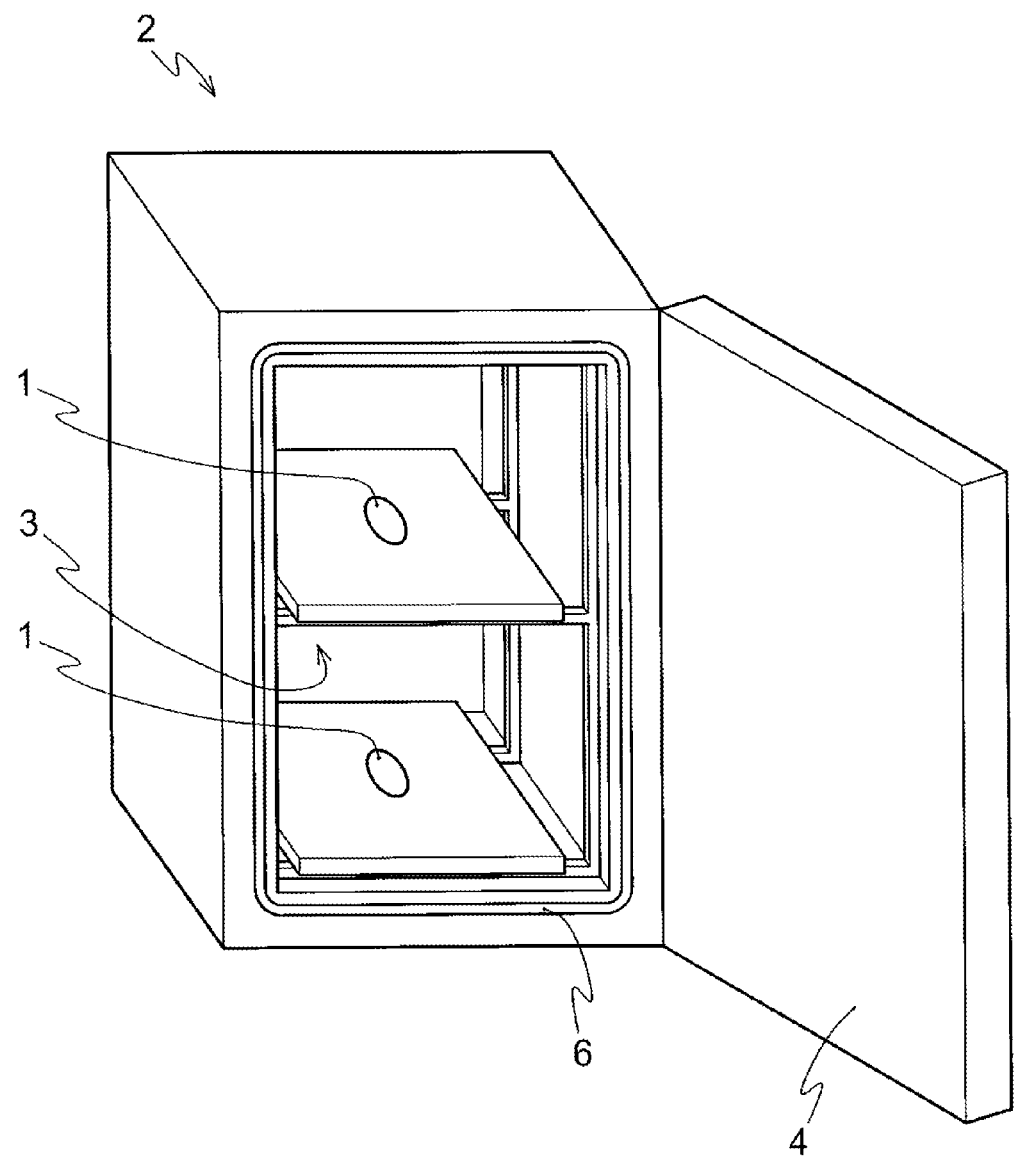
FIG. 1 is an explanatory view illustrating a sterilizing chamber and an item to be sterilized according to an Embodiment of the present invention.
Figure 2:
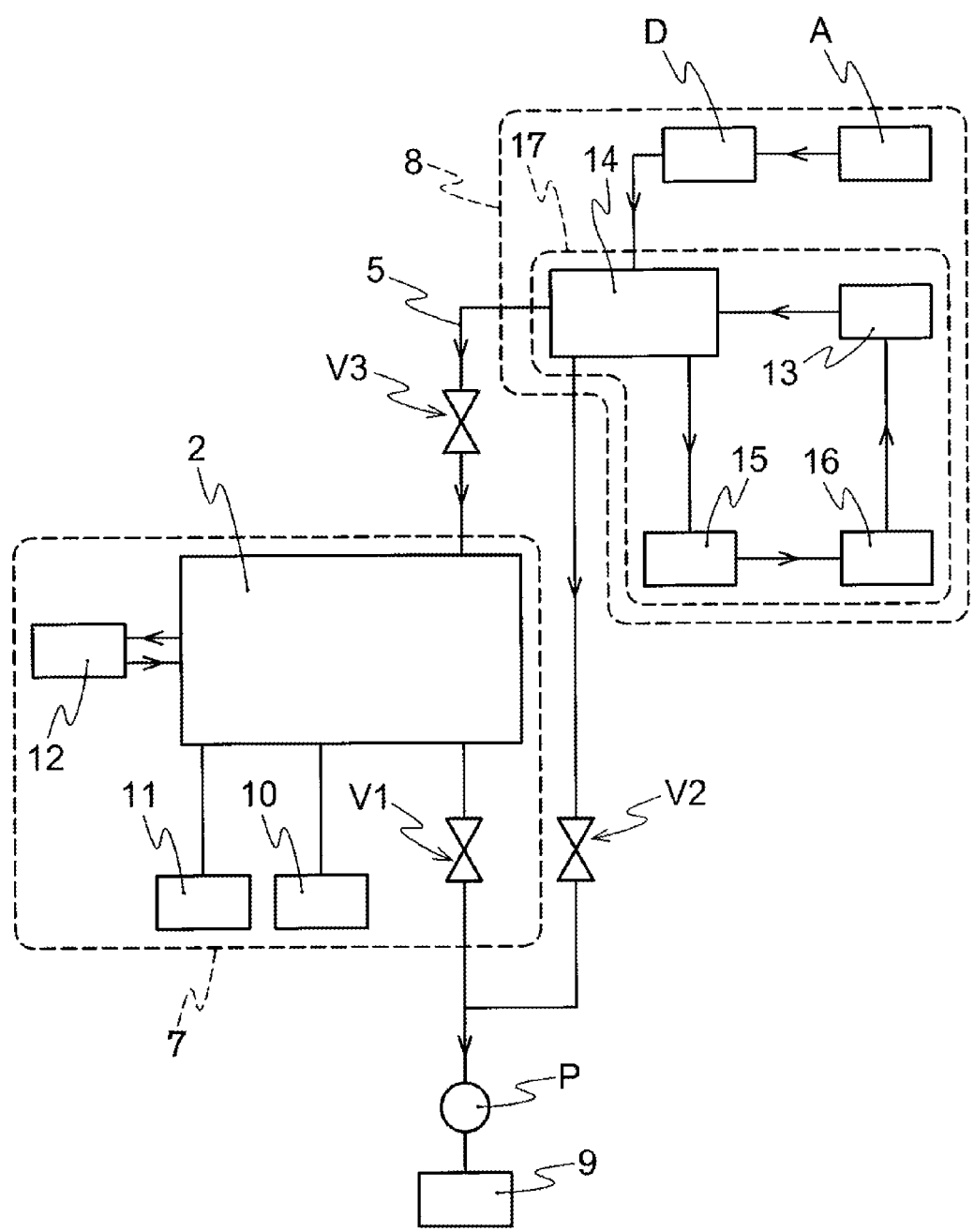
FIG. 2 is an explanatory view illustrating a gas supply system according to an Embodiment of the present invention.

As shown in FIGS. 1 and 2, as for the items 1 to be sterilized, medical instruments such as tubes having a narrow opening with an internal diameter of approximately from 1 to 4 mm, and surgical knives or scissors attached with germs are primarily intended. In addition, such items 1 to be sterilized may be provided for sterilization in a state where the item is contained in a polyethylene bag made partly made by a non-woven breathable materials.

The sterilizing chamber 2 includes an opening 3 for loading/unloading the item 1 to be sterilized, a shielding door 4 capable of sealing the opening 3, and a gas supply opening 5 for introducing a high concentration $NO_2$ gas. The shielding door 4 is provided with a sealing material 6 in the periphery for securing the sealing property. For the sealing material 6 of the present Embodiment, fluorine-containing elastomer is used from the perspective of the pressure tightness and corrosion resistance. It is preferable that the safety is improved when the shielding door 4 is provided with an interlock which does not allow opening the door in the case an $NO_2$ gas concentration in the sterilizing chamber 2 is equal to or more than the level harmful for humans according to measurement of an $NO_2$ sensor.

In the present Embodiment, the sterilizing chamber 2 has a rectangular box shape, however it may have a spherical or cylindrical shape. The internal volume of the chamber is preferably around 10 to 500 L, more preferably around 20 to 300 L, and most preferably around 40 to 200 L. In the case the volume is less than 10 L, elongate medical instruments such as forceps may not fit. On the other hand, in the case the volume is more than 500 L, the size of the entire apparatus increases such that the apparatus may be larger than the widths of such as door openings and elevators, and thus the apparatus may be difficult to be moved. The sterilizing chamber 2 of the present Embodiment has an internal volume of 150 L. The chamber is formed by using such as stainless, nickel-chrome alloy, or unsaturated polyester resin (FRP) which is not likely to be corroded by $NO_2$ or nitric acid, and is stably supported by securing it on a base (not shown).

The sterilizing chamber 2 of the present Embodiment is illustrated by configuring it as a main portion of a sterilizing apparatus 7 for such as medical instruments. In addition to the sterilizing chamber 2, the sterilizing apparatus 7 is configured to include a humidifying apparatus 10 for controlling humidity in the sterilizing chamber 2, a temperature controlling apparatus 11 for controlling a temperature in the sterilizing chamber 2, and a circulating means 12 for dispersing a gas for obtaining a uniform temperature distribution in the sterilizing chamber 2. Furthermore, to the sterilizing apparatus, a gas supply system 8 for supplying a high concentration $NO_2$ gas from the gas supply opening 5 to the inside of the sterilizing chamber 2, and an exhausting apparatus 9 for vacuuming the sterilizing chamber 2 are connected.

The exhausting apparatus 9 is formed by connecting a control valve V1 and a pump P to the sterilizing chamber 2. In the case of exhausting an $NO_2$ gas used in a previous step, an exhaust gas treatment means also needs to be provided for making the remaining $NO_2$ gas to be harmless. In the present Embodiment, an exhaust gas treatment means including an ozonizer and nitric acid filter is provided. In the exhaust gas treatment means, ozone generated by the ozonizer is reacted with $NO_2$ to generate dinitrogen pentoxide ($N_2O_5$), and subsequently the dinitrogen pentoxide and nitric acid generated in the sterilizing chamber 2 are adsorbed by the nitric acid filter.

The humidifying apparatus 10 is configured by communicating an evaporation portion with the sterilizing chamber 2, the evaporation portion including a stainless steel pipe around which an electric heater is wrapped and an insulating material covers thereon. Vapor, which is generated by filling water in the evaporation portion heated to approximately from 50 to 80° C. by heating with the electric heater, is introduced in the sterilizing chamber 2 under a decreased pressure to humidify the sterilizing chamber 2. In the present Embodiment, the sterilizing chamber 2 under an absolute dry state created by vacuuming is humidified such that an amount of water vapor can be accurately measured by measuring a value of pressure increase due to the humidification with a pressure sensor in the sterilizing chamber 2. By linking with the measured value, the humidity in the sterilizing chamber 2 is controlled by controlling the heating level of the electric heater and an amount of water to be filled. In the present Embodiment, it is noted that a number of stainless steel pellets are filled in the stainless steel pipe. With that configuration, it is preferable that heat capacity increases, and thus humidification capacity increases.

The temperature controlling apparatus 11 is configured in such a manner that a rubber heater is adhered to an outer circumference of the sterilizing chamber 2. A current value of the rubber heater is controlled by the information from a thermocouple attached thereto, and the inside of the sterilizing chamber 2 can be controlled to a desired level of temperature of from approximately 10 to 90° C., for example.

A circulating means 12 is provided for the purpose of suppressing variations of the $NO_2$ gas concentration and relative humidity caused by temperature differences by reducing the difference of the ambient temperatures in the sterilizing chamber 2. In the present Embodiment, the circulating means is configured in such a manner that the high concentration $NO_2$ gas taken from the sterilizing chamber 2 circulates back into the sterilizing chamber 2 via a bellows pump. In addition to this, the high concentration $NO_2$ gas may be uniformly circulated by utilizing the convection phenomenon of the high concentration $NO_2$ gas heated by the temperature controlling apparatus 11. Alternatively, the inside temperature may be uniformed by providing a fan in the sterilizing chamber 2.

In the present Embodiment, the gas supply system 8 utilizes a high concentration $NO_2$ gas generating system as shown in FIG. 2. The high concentration $NO_2$ gas generating system is configured to include a chamber 14, a flow resistive portion 15 connected to the chamber 14 at the downstream side of the path via a pipe, a plasma generator 16 connected to the flow resistive portion 15 at the downstream side of the path via a pipe, and a circulating apparatus 13 connected to the plasma generator 16 at the downstream side of the path via a pipe. The circulating apparatus 13 is further connected to the chamber 14 at the upstream side of the path via a pipe such that a cyclic circulating path 17 is formed by the chamber 14, flow resistive portion 15, plasma generator 16, and circulating apparatus 13. By the operation of the circulating apparatus 13, a gas mixture including nitrogen and oxygen circulates in the circulating path 17 to generate $NO_2$. The reference numeral A shows an air inlet portion, and the reference numeral D shows a gas drying means. The chamber 14 is further connected to a control valve V2 and pump P as well as to the exhausting apparatus 9.

The chamber 14 of the present Embodiment is a gas container for temporarily storing the generated high concentration $NO_2$ gas, and is connected to the gas supply opening 5 of the sterilizing chamber 2 via a supply pipe provided with a control valve V3. The chamber 14 is formed to have a size of one half to one tenth of the sterilizing chamber 2, and the chamber 14 in the present Embodiment has a volume of 40 L. The gas mixture is a gas including nitrogen and oxygen which are ingredients for generating the high concentration $NO_2$ gas, and dry air is employed as the gas mixture in the present Embodiment.

An intense electric field is formed in a plasma generating portion of the plasma generator 16. Nitrogen and oxygen of the gas mixture generate dielectric breakdown by being excited through the intense electric field, and are displaced from the molecular state to the low-temperature (non-equilibrium plasma) state. The gas under the low-temperature state has a high reactivity with respect to other gases under the low-temperature state or molecular state. Therefore, when the gas mixture including primarily nitrogen and oxygen is introduced to the plasma generating portion, a portion thereof is converted to nitrogen oxides of such as nitrogen monoxide and nitrogen dioxide or to ozone. Since the pressure of the circulating gas mixture (NOx gas mixture) decreases when it passes through the flow resistive portion 15, the gas mixture can be displaced to the low-temperature plasma state more stably in the plasma generator 16.

$$N_2+O_2 \rightarrow 2NO \qquad 1.$$

$$N_2+2O_2 \rightarrow 2NO_2 \qquad 2.$$

$$3O_2 \rightarrow 2O_3 \qquad 3.$$

It is noted that the conversion ratio is the largest in the case of equation 1. A portion of NO generated according to equation 1 binds with oxygen under the low-temperature plasma state in the plasma generating portion and is converted to $NO_2$.

$$2NO+O_2 \rightarrow 2NO_2 \qquad 4.$$

The NOx gas mixture including $NO_2$ thus generated circulates through the circulating path 17 by applying pressure thereon with the circulating apparatus 13 or is retained in the chamber 14. During this time, NO generated according to equation 1 reacts stepwise with oxygen in the NOx gas mixture or with the ozone generated according to equation 3, and is further converted to $NO_2$ as shown in equations 5 and 6. As a result, the $NO_2$ concentration increases.

$$2NO+O_2 \rightarrow 2NO_2 \qquad 5.$$

$$NO+O_3 \rightarrow NO_2+O_2 \qquad 6.$$

Ozone generated according to equation 3 reacts with nitrogen in the NOx gas mixture to generate NO.

$$N_2+2O_3 \rightarrow 2NO+2O_2 \qquad 7.$$

This NO is also converted to $NO_2$ by the reactions according to equations 5 and 6.

In this manner, in the course the dry gas mixture circulates in the circulating path 17 by the operation of the circulating apparatus 13, an NOx gas mixture including NO and $NO_2$ is generated by the reaction of nitrogen and oxygen displaced to the low-temperature plasma (non-equilibrium plasma) state when passing through the plasma generator 16. The NO is converted to $NO_2$ by reacting with oxygen in the NOx gas mixture and ozone, and the concentration of $NO_2$ gradually increases. As a result, the high concentration $NO_2$ gas with the $NO_2$ concentration of from 5,000 to 100,000 ppm is generated.

The high concentration $NO_2$ gas thus generated is supplied from the gas supply opening 5 to the sterilizing chamber 2 via the supply pipe. In this specification, the gas including NOx which is generated by having circulating the gas mixture through the plasma generator at least once is referred to as the NOx gas mixture.

The sterilization method of the present Embodiment is performed by using the sterilizing apparatus 7, and is characterized in that the inside of the sterilizing chamber 2 containing the item 1 to be sterilized is humidified, and the high concentration $NO_2$ gas is filled therein to obtain an $NO_2$ concentration of from 9 to 100 mg/L in the sterilizing chamber 2. Specifically, it includes the steps of:

(1) setting an item 1 to be sterilized in the sterilizing chamber 2 (setting step), (2) exhausting the air inside to vacuum the inside of the sterilizing chamber 2 (vacuuming step), (3) humidifying the inside of the sterilizing chamber 2 (humidifying step), (4) performing sterilization by filling the high concentration $NO_2$ gas in the sterilizing chamber 2 (sterilizing step), (5) exhausting the high concentration $NO_2$ gas in the sterilizing chamber 2 (gas exhausting step), and
(6) taking out the sterilized item 1 in the sterilizing chamber 2 (taking out step).

In the setting step, the shielding door 4 of the sterilizing chamber 2 is opened, and the item 1 to be sterilized is placed by inserting it from the opening 3 to the inside. In order not to prevent the contact with the high concentration $NO_2$ gas, the item 1 to be sterilized may be suitably placed on a placement table in accordance with its shape. In the case a plurality of items 1 to be sterilized is sterilized at the same time, shelves may be arranged in such a manner that they do not overlap each other, and the items are placed thereon.

In the vacuuming step, the pressure of the inside of the sterilizing chamber 2 is decreased through discharging the air in the chamber by driving the pump P of the exhausting apparatus. Through this depressurization, the air in detailed and innermost portions such as a hole of the item 1 to be sterilized is discharged. When the high concentration $NO_2$ gas is filled in the later sterilizing step, the $NO_2$ gas thus quickly enters into the innermost detailed portions such as a hole of the item to be sterilized. As a result, the reliability of sterilization increases.

The level of the exhaustion is preferably from approximately 0.01 KPa to 1 KPa (absolute pressure), more preferably from 0.1 KPa to 1 KPa (absolute pressure), and the pressure is decreased to approximately 0.5 KPa (absolute pressure) in the present Embodiment. When the pressure is less than 0.01 KPa (absolute pressure), the exhaustion is excessive, and the operating time and costs are likely to increase. On the other hand, when the pressure is above 1 KPa (absolute pressure), penetration of the vapor or $NO_2$ gas into the detail portions is likely to be insufficient, and this may lead to the decreased reliability of the sterilization effect.

The humidifying step is performed by supplying vapor in the sterilizing chamber 2 using the humidifying apparatus 10. The vapor permeates the innermost detail portions of such as a hole of the item 1 to be sterilized through the humidifying step, and the high concentration $NO_2$ gas is filled under this state. The humidity and $NO_2$ concentration suitable for sterilization can be obtained over the detailed and innermost portions of the item 1 to be sterilized, and the reliability of the sterilization is preferably increased as a result. The combination of a sufficient humidity and $NO_2$ concentration accelerates the generation of nitric acid over the surface of a germ, and is considered to increase the effect of sterilization. In addition to this, the high concentration $NO_2$ gas is filled after the humidification in the present Embodiment. With that, in accordance with the pressure increase occurring when the high concentration $NO_2$ gas is filled in the sterilizing chamber 2, the $NO_2$ enters into the detailed and innermost portions of the already humidified item 1 to be sterilized, and the nitrification of $NO_2$ is accelerated. As a result, the sterilization effect is further effectively achieved. In the present Embodiment, the humidification is performed under the decreased pressure through the evacuation. The generation of the vapor is therefore obtained in the humidifying apparatus 10 at a relatively low temperature.

The level of humidification is such that the relative humidity is from 10 to 90% R.H., more preferably from 20 to 60% R.H., and approximately 30% R.H. in the present Embodiment. In the case the relative humidity is less than 10% R.H., sufficient nitrification cannot be obtained. This may lead to the decreased reliability of sterilization, and the efficiency of the sterilization operation is likely to decrease since the duration of sterilization which is required for sterilization becomes considerably long. It is speculated that this occurs because sufficient nitrification cannot be obtained. On the other hand, in the case the relative humidity is above 90% R.H., nitrification is excessively promoted due to the excessive vapor, and the item 1 to be sterilized may be damaged as a result.

In the sterilizing step, the item 1 to be sterilized is sterilized by filling the high concentration $NO_2$ gas in the sterilizing chamber 2 and maintaining it for a specific time. As mentioned above, by filling the high concentration $NO_2$ gas with the $NO_2$ concentration from 5,000 to 100,000 ppm, the $NO_2$ concentration in the sterilizing chamber 2 is made to be from 9 to 100 mg/L, more preferably from 20 to 80 mg/L, and from 20 to 40 mg/L in the present Embodiment. In the case the $NO_2$ concentration is less than 9 mg/L, a sufficient sterilization effect required for any germs cannot be obtained. On the other hand, in the case the concentration is above 100 mg/L, significant difference in shortening the sterilization time is not expected above such concentration, and rather, a problem associated with the exhaust gas treatment becomes troublesome.

Although, the duration of sterilization is different depending on the factors such as the $NO_2$ concentration in the sterilizing chamber 2 and types of items 1 to be sterilized, the sterilization is preferably maintained from 10 to 480 minutes. In the case the duration is less than 10 minutes, a sufficient sterilization effect required for any germs cannot be obtained. On the other hand, in the case the duration is generally over 480 minutes, there is no significant difference in sterilization effect over such duration, and the processing time is likely to be unnecessarily prolonged.

In the present Embodiment, the high concentration $NO_2$ gas which is generated by the high concentration $NO_2$ gas generating system employed as the gas supply system 8 and is stored in the chamber 14 is introduced in the sterilizing chamber 2 to perform the sterilizing step. However, as mentioned above, the volume of the chamber 14 is 40 L and is only one forth of that of the sterilizing chamber 2. Accordingly, in the present Embodiment, the high concentration $NO_2$ gas stored in the chamber 14 is firstly introduced in the exhausted sterilizing chamber 2 by opening the control valve V3 of the supply pipe. With that, $NO_2$ is diffused in the sterilizing chamber 2, and the internal pressure of the sterilizing chamber 2 slightly increases. Subsequently, the high concentration $NO_2$ gas generating system is again operated to store the high concentration $NO_2$ gas in the chamber 14. When the gas is again introduced in the sterilizing chamber 2, the amount of $NO_2$ and the internal pressure in the sterilizing chamber 2 gradually increase. In the present Embodiment, the method in which the high concentration $NO_2$ gas is filled in the sterilizing chamber 2 by repeating such operation for several times is employed. The chamber 14 can be made to be compact by employing such system, and a sterilizing apparatus incorporating a relatively compact high concentration $NO_2$ gas generating system can be configured. As a result, many advantages can be realized such as that the apparatus may be used in a small space in a hospital or the like, or the apparatus may be moved within a hospital using an elevator in a relatively easy manner.

In the sterilizing step of the present Embodiment, the pressure in the sterilizing chamber 2 at the time of finally completing the filling of the $NO_2$ in the sterilizing chamber 2 is made to be such that the pressure difference relative to the external pressure is approximately from −1 KPa to −95 KPa (relative pressure), more preferably approximately from −5 KPa to −70 PKa (relative pressure), and from −30 KPa to −60 KPa (relative pressure) in the present Embodiment. In the case the pressure difference is more than the atmospheric pressure, the $NO_2$ gas may leak through such as the opening 3 of the sterilizing chamber 2 or the pipe joint. Therefore, it is preferable that the pressure difference is safely to be −1 kPa or less. On the other hand, in the case the pressure difference is above −95 KPa (relative pressure), it is excessive for the purpose of preventing gas leakage, and a sufficient sterilization effect might not be able to be obtained since the amount of $NO_2$ which can be introduced in the sterilizing chamber 2 is likely to decrease.

In the present Embodiment, by controlling the temperature controlling apparatus 11, the ambient temperature in the sterilizing chamber 2 during the sterilizing step is adjusted to be preferably from 10° C. to 90° C., more preferably from 30° C. to 60° C., and 50° C. in the present Embodiment. In the case the temperature is below 10° C., moisture supply exhibiting the sterilization effect like $NO_2$ is likely to be insufficient due to the small amount of saturated vapor, and this may lead to the decrease of the sterilizing action (it is speculated this occurs due to insufficient nitrification). In addition, a temperature of 10° C. or above is preferable from the perspective of preventing dew condensation. On the other hand, in the case the temperature is above 90° C., items 1 to be sterilized with low a heat resistance property like plastic materials may be deformed or change in color. In addition, it is not preferably since the time for gas exhaustion after completing the sterilization takes longer.

In the present Embodiment, by the circulating apparatus 12, the temperature difference in the sterilizing chamber 2 is controlled preferably to be 20° C. or less, more preferably to be 15° C. or less, and 10° C. in the present Embodiment by gently dispersing the flow of the $NO_2$ gas in the sterilizing chamber 2 during the sterilizing step. In the case the temperature difference in the sterilizing chamber 2 is over 15° C., distributions of vapor, $NO_2$, and nitric acid becomes uneven, and this may lead to variations in the sterilization effect.

After completing the sterilizing step performed for a predetermined time, the gas exhausting step is performed. In the gas exhausting step of the present Embodiment, the $NO_2$ gas remaining in the sterilizing chamber 2 is made to be harmless by an exhausted gas treatment means and is exhausted to the outside by staring the exhausting apparatus 9 and pump P.

Subsequently in the taking out step, after confirming that the $NO_2$ gas remaining in the sterilizing chamber 2 becomes a low concentration of approximately 0.0017 mg/L or below, for example, by an $NO_2$ sensor provided in a subsequent part of the exhaust gas treatment means, the shielding door 4 of the sterilizing chamber 2 is opened to take out the sterilized item 1.

Another Embodiment is illustrated. The present Embodiment illustrates a sterilization method of tubes having a narrow opening with an internal diameter of approximately from 1 to 4 mm. A narrow opening of tubes generally has a length from 0.2 to 2 m. In order for the $NO_2$ gas to reach inside through from an end of a narrow opening, a higher level of control is required. In the present Embodiment, the relative humidity in the sterilizing chamber 2 is firstly controlled to from 20 to 50% R.H. By filling the high concentration $NO_2$ gas in the sterilizing chamber 2 under such condition, the concentration of $NO_2$ in the sterilizing chamber 2 is to be from 20 to 40 mg/L. In the case the relative humidity is less than 20% R.H., sufficient moisture may not be achieved in a narrow opening of tubes (sufficient nitrification might not be able to be achieved). On the other hand, in the case the relative humidity is above 90% R.H., the dew condensation water which is generated in a narrow opening of tubes may block the narrow opening to prevent the introduction of the $NO_2$ gas.

After such sterilizing condition is maintained for between 10 and 480 minutes, the $NO_2$ gas is exhausted to complete the sterilization. In the present Embodiment, due to the need for securing the reliability of the sterilization of an inside of significantly elongated tubes, the duration of sterilization requires a minimum of 60 minutes. However, the duration of sterilization over 480 minutes is excessive from the perspective of the sterilization effect.

A further alternative Embodiment is illustrated. The present Embodiment illustrates a sterilization method of surgical scissors whose opposing surfaces crossover. Since scissors are sterilized in a state where a pair of blades with germs crossovers while having a space of a few micrometers between them, a higher level of control is required. In the present Embodiment, the relative humidity in the sterilizing chamber 2 is firstly controlled to from 20 to 50% R.H. By filling the high concentration $NO_2$ gas in the sterilizing chamber 2 under such condition, the concentration of $NO_2$ in the sterilizing chamber 2 is to be from 20 to 40 mg/L. In the case the relative humidity is less than 10% R.H., sufficient moisture may not be achieved in the crossover portion of the blades of surgical scissors (sufficient nitrification might not be able to be achieved). On the other hand, in the case the relative humidity is above 90% R.H., the dew condensation water may block the crossover portion of the blades to prevent the introduction of the $NO_2$ gas. In addition, in the case the $NO_2$ concentration is less than 10 mg/L, the sterilization effect is likely to be insufficient for germs present in a space with a few micrometers. On the other hand, in the case the concentration is above 100 mg/L, significant difference in the sterilization effect is not obtained above such concentration. Furthermore, the problem associated with the exhaust gas treatment becomes troublesome since the amount of the remaining $NO_2$ for exhaustion is increased.

After such sterilizing condition is maintained for between 10 and 480 minutes, the $NO_2$ gas is exhausted to complete the sterilization. In the present Embodiment, since $NO_2$ is introduced in the space with a few micrometers to exert the sterilization effect, the duration of sterilization requires a minimum of 30 minutes. However, the duration of sterilization over 480 minutes is excessive from the perspective of the sterilization effect.

EXAMPLE

Hereinafter, the sterilization method of the present invention is described in detail by way of Examples, however the present invention is not limited to those Examples.
(Availability of sterilization in the case of changing relative humidity, concentration of high concentration $NO_2$ gas, and duration of sterilization)

Example 1-1

Glass fiber patches (10 mm diameter, 1 mm thickness) planted with over a million germs (*Geobacillus stearothermophilus*) were enclosed in a polyethylene nonwoven pouch and placed in a sterilizing chamber. The inside air was discharged to vacuum the inside of the sterilizing chamber. The inside of the sterilizing chamber is humidified to obtain 10% RH. The temperature in the sterilizing chamber was made to be 50° C., and $NO_2$ was filled in the sterilizing chamber to obtain a concentration of 14.4 mg/L by using a prepared $NO_2$ gas cylinder with a high concentration $NO_2$ gas (15 kppm concentration). Sterilization was performed for 5 minutes. At this time, the concentration in the sterilizing chamber reached 56 kPa (absolute pressure) by filling the high concentration $NO_2$ gas. After sterilization, the high concentration $NO_2$ gas in the sterilizing chamber was discharged, and sterilized item was taken out.

The number of sterilized glass fiber patches was counted. The result is shown in Table 1.

Examples 1-2 to 1-4

Other than the duration of sterilization was set to be 10 minutes, 20 minutes, and 30 minutes, respectively, sterilization was performed in the same manner as in Example 1-1. The result is shown in Table 1.

Example 1-5

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 1-1. The result is shown in Table 1.

Examples 1-6 to 1-8

Other than the duration of sterilization was set to be 10 minutes, 20 minutes, and 30 minutes, respectively, sterilization was performed in the same manner as in Example 1-5. The result is shown in Table 1.

Example 1-9

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 1-1. The result is shown in Table 1.

Examples 1-10 to 1-12

Other than the duration of sterilization was set to be 10 minutes, 20 minutes, and 30 minutes, respectively, sterilization was performed in the same manner as in Example 1-9. The result is shown in Table 1.

Example 2-1

Other than the relative humidity was made to be 20% during sterilization, sterilization was performed in the same manner as in Example 1-1. The result is shown in Table 1.

Examples 2-2 to 2-4

Other than the duration of sterilization was set to be 10 minutes, 20 minutes, and 30 minutes, respectively, sterilization was performed in the same manner as in Example 2-1. The result is shown in Table 1.

Example 2-5

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 2-1. The result is shown in Table 1.

Examples 2-6 to 2-8

Other than the duration of sterilization was set to be 10 minutes, 20 minutes, and 30 minutes, respectively, sterilization was performed in the same manner as in Example 2-5. The result is shown in Table 1.

Example 2-9

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 2-1. The result is shown in Table 1.

Examples 2-10 to 2-12

Other than the duration of sterilization was set to be 10 minutes, 20 minutes, and 30 minutes, respectively, sterilization was performed in the same manner as in Example 2-9. The result is shown in Table 1.

Example 3-1

Other than the relative humidity was made to be 25% during sterilization, sterilization was performed in the same manner as in Example 1-1. The result is shown in Table 1.

Examples 3-2 to 3-4

Other than the duration of sterilization was set to be 10 minutes, 20 minutes, and 30 minutes, respectively, sterilization was performed in the same manner as in Example 3-1. The result is shown in Table 1.

Example 3-5

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 3-1. The result is shown in Table 1.

Examples 3-6 to 3-8

Other than the duration of sterilization was set to be 10 minutes, 20 minutes, and 30 minutes, respectively, sterilization was performed in the same manner as in Example 3-5. The result is shown in Table 1.

Example 3-9

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 3-1. The result is shown in Table 1.

Examples 3-10 to 3-12

Other than the duration of sterilization was set to be 10 minutes, 20 minutes, and 30 minutes, respectively, sterilization was performed in the same manner as in Example 3-9. The result is shown in Table 1.

Example 4-1

Other than the relative humidity was made to be 30% during sterilization, sterilization was performed in the same manner as in Example 1-1. The result is shown in Table 1.

Examples 4-2 to 4-4

Other than the duration of sterilization was set to be 10 minutes, 20 minutes, and 30 minutes, respectively, sterilization was performed in the same manner as in Example 4-1. The result is shown in Table 1.

Example 4-5

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 4-1. The result is shown in Table 1.

Examples 4-6 to 4-8

Other than the duration of sterilization was set to be 10 minutes, 20 minutes, and 30 minutes, respectively, sterilization was performed in the same manner as in Example 4-5. The result is shown in Table 1.

Example 4-9

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 4-1. The result is shown in Table 1.

Examples 4-10 to 4-12

Other than the duration of sterilization was set to be 10 minutes, 20 minutes, and 30 minutes, respectively, sterilization was performed in the same manner as in Example 4-9. The result is shown in Table 1.

Comparative Example 1-1

Figure 3:
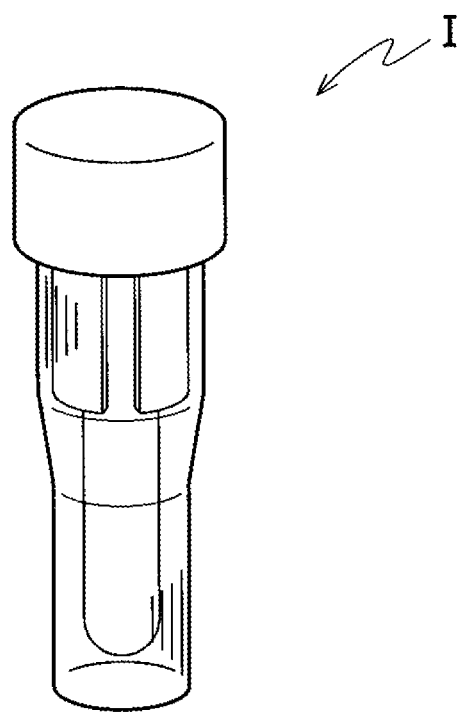
FIG. 3 is a drawing of an SCBI used in Example 1-1 of the present invention.

20 of an SCBI (Self Contained Biological Indicator) (see reference numeral I of FIG. 3) including glass fiber patches (10 mm diameter, 1 mm thickness) planted with over a million germs (*Geobacillus stearothermophilus*) were set in the sterilizing chamber. A relative humidity during sterilization was 0%, and $NO_2$ was filled in the sterilizing chamber to obtain a concentration of 38.4 mg/L by using a prepared $NO_2$ gas cylinder with a high concentration $NO_2$ gas (40 kppm concentration). Other than those, sterilization was performed in the same manner as in Example 1-2. The result is shown in Table 2.

It is noted that the SCBI was determined to be sterilized by immersing the SCBI in a special culture solution and determining the presence/absence of change in colors or opacity. In addition, commercially available cylinders with a precise concentration were used in order to increase the reproducibility of the data.

Comparative Example 1-2

Other than that the duration of sterilization was 20 minutes, sterilization was performed in the same manner as in Comparative Example 1-1. The result is shown in Table 2.

Comparative Example 1-3

Other than that the duration of sterilization was 30 minutes, sterilization was performed in the same manner as in Comparative Example 1-1. The result is shown in Table 2.

Comparative Example 2-1

20 of an SCBI including glass fiber patches (10 mm diameter, 1 mm thickness) planted with over a million germs (*Geobacillus stearothermophilus*) were set in the sterilizing chamber. A relative humidity during sterilization was 0%, and $NO_2$ was filled in the sterilizing chamber to obtain a concentration of 62 mg/L by using a prepared $NO_2$ gas cylinder with a high concentration $NO_2$ gas (65 kppm concentration). Other than those, sterilization was performed in the same manner as in Example 1-2. The result is shown in Table 2.

Comparative Example 2-2

Other than that the duration of sterilization was 20 minutes, sterilization was performed in the same manner as in Comparative Example 2-1. The result is shown in Table 2.

Comparative Example 2-3

Other than that the duration of sterilization was 30 minutes, sterilization was performed in the same manner as in Comparative Example 2-1. The result is shown in Table 2.

TABLE 1

|  | Temperature | Pressure | Relative humidity | $NO_2$ concentration | Time | Result | |
|---|---|---|---|---|---|---|---|
| Example 1-1 | 50° C. | 56 kPa | 10% RH | 15 kppm | 5 min | 0/10 | never |
| Example 1-2 |  |  |  |  | 10 min | 0/10 | never |
| Example 1-3 |  |  |  |  | 20 min | 1/10 | hardly |
| Example 1-4 |  |  |  |  | 30 min | 9/10 | almost |
| Example 1-5 |  |  |  | 18 kppm | 5 min | 0/10 | never |
| Example 1-6 |  |  |  |  | 10 min | 0/10 | never |
| Example 1-7 |  |  |  |  | 20 min | 3/10 | hardly |
| Example 1-8 |  |  |  |  | 30 min | 7/10 | almost |
| Example 1-9 |  |  |  | 21 kppm | 5 min | 0/10 | never |
| Example 1-10 |  |  |  |  | 10 min | 0/10 | never |
| Example 1-11 |  |  |  |  | 20 min | 5/10 | hardly |
| Example 1-12 |  |  |  |  | 30 min | 8/10 | almost |
| Example 2-1 | 50° C. | 56 kPa | 20% RH | 15 kppm | 5 min | 10/10 | never |
| Example 2-2 |  |  |  |  | 10 min | 7/10 | almost |
| Example 2-3 |  |  |  |  | 20 min | 10/10 | perfect |
| Example 2-4 |  |  |  |  | 30 min | 10/10 | perfect |
| Example 2-5 |  |  |  | 18 kppm | 5 min | 1/10 | hardly |
| Example 2-6 |  |  |  |  | 10 min | 8/10 | almost |
| Example 2-7 |  |  |  |  | 20 min | 9/10 | almost |
| Example 2-8 |  |  |  |  | 30 min | 10/10 | perfect |
| Example 2-9 |  |  |  | 21 kppm | 5 min | 1/10 | hardly |
| Example 2-10 |  |  |  |  | 10 min | 9/10 | almost |

TABLE 1-continued

| | Temperature | Pressure | Relative humidity | NO$_2$ concentration | Time | Result | |
|---|---|---|---|---|---|---|---|
| Example 2-11 | | | | | 20 min | 10/10 | perfect |
| Example 2-12 | | | | | 30 min | 9/10 | almost |
| Example 3-1 | 50° C. | 56 kPa | 25% RH | 15 kppm | 5 min | 5/10 | hardly |
| Example 3-2 | | | | | 10 min | 7/10 | almost |
| Example 3-3 | | | | | 20 min | 10/10 | perfect |
| Example 3-4 | | | | | 30 min | 10/10 | perfect |
| Example 3-5 | | | | 18 kppm | 5 min | 3/10 | hardly |
| Example 3-6 | | | | | 10 min | 10/10 | perfect |
| Example 3-7 | | | | | 20 min | 10/10 | perfect |
| Example 3-8 | | | | | 30 min | 10/10 | perfect |
| Example 3-9 | | | | 21 kppm | 5 min | 7/10 | almost |
| Example 3-10 | | | | | 10 min | 10/10 | perfect |
| Example 3-11 | | | | | 20 min | 10/10 | perfect |
| Example 3-12 | | | | | 30 min | 10/10 | perfect |
| Example 4-1 | 50° C. | 56 kPa | 30% RH | 15 kppm | 5 min | 0/10 | never |
| Example 4-2 | | | | | 10 min | 9/10 | almost |
| Example 4-3 | | | | | 20 min | 10/10 | perfect |
| Example 4-4 | | | | | 30 min | 10/10 | perfect |
| Example 4-5 | | | | 18 kppm | 5 min | 0/10 | never |
| Example 4-6 | | | | | 10 min | 8/10 | almost |
| Example 4-7 | | | | | 20 min | 10/10 | perfect |
| Example 4-8 | | | | | 30 min | 10/10 | perfect |
| Example 4-9 | | | | 21 kppm | 5 min | 10/10 | perfect |
| Example 4-10 | | | | | 10 min | 10/10 | perfect |
| Example 4-11 | | | | | 20 min | 10/10 | perfect |
| Example 4-12 | | | | | 30 min | 10/10 | perfect |

TABLE 2

| | Temperature | Pressure | Relative humidity | NO$_2$ concentration | Time | Result | |
|---|---|---|---|---|---|---|---|
| Com. Ex. 1-1 | 50° C. | 56 kPa | 0% RH | 40 kppm | 10 min | 0/20 | never |
| Com. Ex. 1-2 | | | | | 20 min | 0/20 | never |
| Com. Ex. 1-3 | | | | | 30 min | 1/20 | hardly |
| Com. Ex. 2-1 | | | | 65 kppm | 10 min | 0/20 | never |
| Com. Ex. 2-2 | | | | | 20 min | 2/20 | hardly |
| Com. Ex. 2-3 | | | | | 30 min | 12/20 | hardly |

From the result of Tables 1 and 2, it was found that the sterilization characteristics are significantly improved by humidification. Particularly, it was found that all patches could be sterilized within 30 minutes when the humidity is above 25% RH. In other words, it was found that the sterilization characteristics are higher with higher humidity, the sterilization characteristics are higher with higher NO$_2$ concentration, and the sterilization characteristics are higher with longer duration. Also, under a dry environment, it was found that all patches could not be sterilized in 30 minutes even if a high concentration NO$_2$ gas of 38.4 mg/L or 62 mg/L was used.

Under 30% RH, sterilization is completely performed when the duration is more than 20 minutes. Although tests were not performed under that concentration (14.4 mg/L), the sterilization characteristics are higher when the duration is longer as described above. Accordingly, even if the concentration is low, the higher sterilization characteristics can be realized with the longer duration. In specific, in the case of a high concentration NO$_2$ gas with approximately 9 mg/L, which is ⅔ of the concentration as compared with 14.4 mg/L, high sterilization characteristics can be expected, and such gas can be suitable employed for sterilization.

(Availability of sterilization in the case an item to be sterilized has a complex configuration)

Example 5-1

Figure 4:
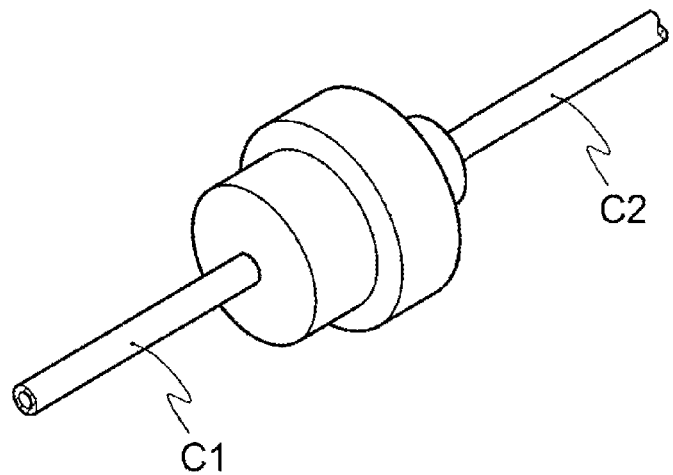
FIG. 4 is a drawing of a tube used in Example 5-1 of the present invention.
Figure 5:
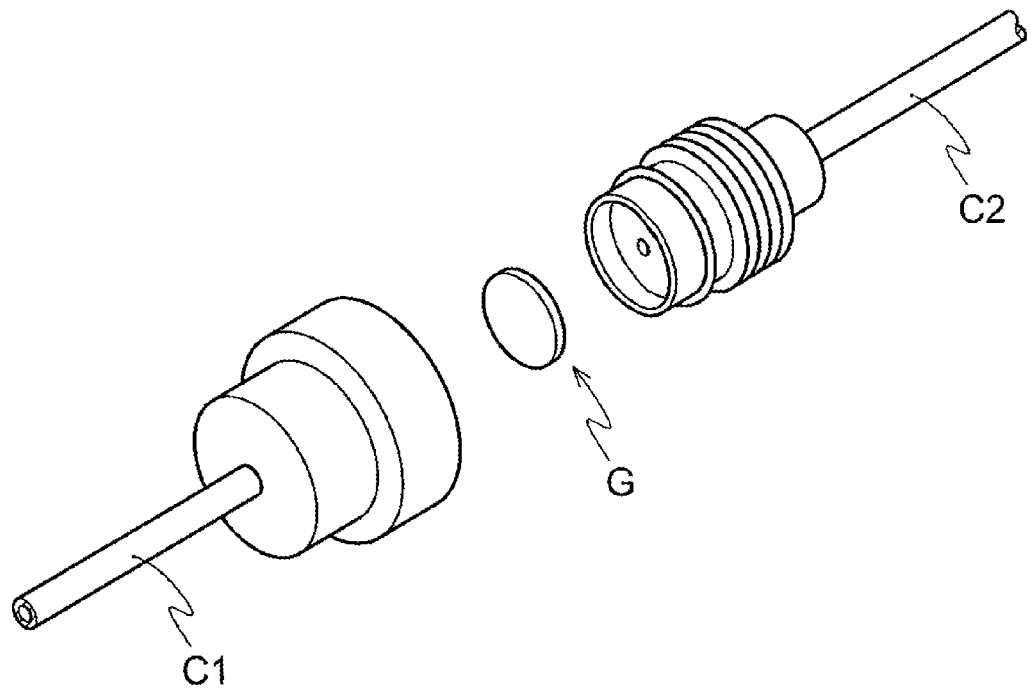
FIG. 5 is a view of a tube used in Example 5-1 of the present invention.

A glass fiber patch G (10 mm diameter, 1 mm thickness) planted with over a million germs (*Geobacillus stearothermophilus*) was held in a center portion of each of two tubes C1 and C2 (1 mm diameter, 125 mm length) shown in FIGS. 4 and 5, and 10 tubes were placed in the sterilizing chamber. The inside air was discharged to vacuum the inside of the sterilizing chamber. The inside of the sterilizing chamber is humidified to obtain 25% RH. The temperature in the sterilizing chamber was made to be 50° C., and NO$_2$ was filled in the sterilizing chamber to obtain a concentration of 14.4 mg/L by using a prepared NO$_2$ gas cylinder with a high concentration NO$_2$ gas (15 kppm concentration). Sterilization was performed for 10 minutes. At this time, the concentration in the sterilizing chamber reached 56 kPa (absolute pressure) by filling the high concentration NO$_2$ gas. After sterilization, the high concentration NO$_2$ gas in the sterilizing chamber was discharged, and sterilized item was taken out. The number of sterilized tubes was counted. The result is shown in Table 3.

It is noted that the tube was determined to be sterilized by immersing the tubes in a special culture solution and determining the presence/absence of change in colors or opacity.

Examples 5-2 to 5-6

Other than the duration of sterilization was set to be 20 minutes, 30 minutes, 40 minutes, 50 minutes, and 60 minutes, respectively, sterilization was performed in the same manner as in Example 5-1. The result is shown in Table 3.

Example 5-7

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 5-1. The result is shown in Table 3.

Examples 5-8 to 5-12

Other than the duration of sterilization was set to be 20 minutes, 30 minutes, 40 minutes, 50 minutes, and 60 minutes respectively, sterilization was performed in the same manner as in Example 5-1. The result is shown in Table 3.

Example 5-13

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 5-1. The result is shown in Table 3.

Examples 5-14 to 5-17

Other than the duration of sterilization was set to be 20 minutes, 30 minutes, 40 minutes, 50 minutes, and 60 minutes, respectively, sterilization was performed in the same manner as in Example 5-13. The result is shown in Table 3.

Example 6-1

Other than that a tube with 2 mm diameter and 125 mm length was used, and the duration of sterilization was 20 minutes, sterilization was performed in the same manner as in Example 5-1. The result is shown in Table 3.

Examples 6-2 and 6-3

Other than the duration of sterilization was set to be 30 minutes and 40 minutes, respectively, sterilization was performed in the same manner as in Example 6-1. The result is shown in Table 3.

Example 6-4

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 6-1. The result is shown in Table 3.

Examples 6-5 and 6-6

Other than the duration of sterilization was set to be 30 minutes and 40 minutes, respectively, sterilization was performed in the same manner as in Example 6-4. The result is shown in Table 3.

Example 6-7

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 6-1. The result is shown in Table 3.

Examples 6-8 and 6-9

Other than the duration of sterilization was set to be 30 minutes and 40 minutes, respectively, sterilization was performed in the same manner as in Example 6-7. The result is shown in Table 3.

Example 7-1

Other than that a tube with a 3 mm diameter and 400 mm length was used, sterilization was performed in the same manner as in Example 5-1. The result is shown in Table 3.

Examples 7-2 to 7-4

Other than the duration of sterilization was set to be 20 minutes, 30 minutes, and 40 minutes, respectively, sterilization was performed in the same manner as in Example 7-1. The result is shown in Table 3.

Example 7-5

Other than $NO_2$ was filled in the sterilizing chamber to obtain a concentration of 17 mg/L by using a prepared $NO_2$ gas cylinder with a high concentration $NO_2$ gas (18 kppm concentration), sterilization was performed in the same manner as in Example 7-1. The result is shown in Table 3.

Examples 7-6 to 7-8

Other than the duration of sterilization was set to be 20 minutes, 30 minutes, and 40 minutes, respectively, sterilization was performed in the same manner as in Example 7-5. The result is shown in Table 3.

Example 7-9

Other than $NO_2$ was filled in the sterilizing chamber to obtain a concentration of 20 mg/L by using a prepared $NO_2$ gas cylinder with a high concentration $NO_2$ gas (21 kppm concentration), sterilization was performed in the same manner as in Example 7-1. The result is shown in Table 3.

Example 7-10

Other than the duration of sterilization was set to be 20 minutes, sterilization was performed in the same manner as in Example 7-9. The result is shown in Table 3.

Example 8-1

A tube with 1 mm diameter and 125 mm length was used, and the tube was enclosed in a polyethylene nonwoven pouch. $NO_2$ was filled in the sterilizing chamber to obtain a concentration of 17 mg/L by using a prepared $NO_2$ gas cylinder with a high concentration $NO_2$ gas (18 kppm concentration). Other than those, sterilization was performed in the same manner as in Example 5-1. The result is shown in Table 4.

Examples 8-2 to 8-7

Other than the duration of sterilization was set to be 20 minutes, 30 minutes, 40 minutes, 50 minutes, 60 minutes, and 70 minutes, respectively, sterilization was performed in the same manner as in Example 8-1. The result is shown in Table 4.

Example 8-8

Other than $NO_2$ was filled in the sterilizing chamber to obtain a concentration of 20 mg/L by using a prepared $NO_2$ gas cylinder with a high concentration $NO_2$ gas (21 kppm concentration), and the duration of sterilization was set to be 30 minutes, sterilization was performed in the same manner as in Example 8-1. The result is shown in Table 4.

Examples 8-9 to 8-12

Other than the duration of sterilization was set to be 40 minutes, 50 minutes, 60 minutes, and 70 minutes, respectively, sterilization was performed in the same manner as in Example 8-8. The result is shown in Table 4.

Example 9-1

A tube with 1 mm diameter and 125 mm length was used, and the tube was enclosed in a polyethylene nonwoven pouch. The relative humidity was 40%, and the duration of sterilization was set to be 40 minutes. $NO_2$ was filled in the sterilizing chamber to obtain a concentration of 17 mg/L by using a prepared $NO_2$ gas cylinder with a high concentration $NO_2$ gas (18 kppm concentration). Other than those, sterilization was performed in the same manner as in Example 5-1. The result is shown in Table 4.

Examples 9-2 to 9-4

Other than the duration of sterilization was set to be 50 minutes, 60 minutes, and 70 minutes, respectively, sterilization was performed in the same manner as in Example 9-1. The result is shown in Table 4.

Example 9-5

Other than $NO_2$ was filled in the sterilizing chamber to obtain a concentration of 20 mg/L by using a prepared $NO_2$ gas cylinder with a high concentration $NO_2$ gas (21 kppm concentration), and the duration of sterilization was set to be 20 minutes, sterilization was performed in the same manner as in Example 9-1. The result is shown in Table 4.

Examples 9-6 to 9-10

Other than the duration of sterilization was set to be 30 minutes, 40 minutes, 50 minutes, 60 minutes, and 70 minutes, respectively, sterilization was performed in the same manner as in Example 9-1. The result is shown in Table 4.

TABLE 3

| | Temperature | Pressure | Relative humidity | $NO_2$ concentration | Time | Result | |
|---|---|---|---|---|---|---|---|
| Example 5-1 | 50° C. | 56 kPa | 25% RH | 15 kppm | 10 min | 0/10 | never |
| Example 5-2 | | | | | 20 min | 0/10 | never |
| Example 5-3 | | | | | 30 min | 0/10 | never |
| Example 5-4 | | | | | 40 min | 0/10 | never |
| Example 5-5 | | | | | 50 min | 0/10 | never |
| Example 5-6 | | | | | 60 min | 4/10 | hardly |
| Example 5-7 | 50° C. | 56 kPa | | 18 kppm | 10 min | 0/10 | never |
| Example 5-8 | | | | | 20 min | 0/10 | never |
| Example 5-9 | | | | | 30 min | 0/10 | never |
| Example 5-10 | | | | | 40 min | 0/10 | never |
| Example 5-11 | | | | | 50 min | 1/10 | hardly |
| Example 5-12 | | | | | 60 min | 10/10 | perfect |
| Example 5-13 | 50° C. | 56 kPa | | 21 kppm | 10 min | 0/10 | never |
| Example 5-14 | | | | | 20 min | 0/10 | never |
| Example 5-15 | | | | | 30 min | 0/10 | never |
| Example 5-16 | | | | | 40 min | 1/10 | hardly |
| Example 5-17 | | | | | 50 min | 8/10 | almost |
| Example 6-1 | 50° C. | 56 kPa | 25% RH | 15 kppm | 20 min | 0/10 | never |
| Example 6-2 | | | | | 30 min | 0/10 | never |
| Example 6-3 | | | | | 40 min | 1/10 | hardly |
| Example 6-4 | 50° C. | 56 kPa | | 18 kppm | 20 min | 0/10 | never |
| Example 6-5 | | | | | 30 min | 0/10 | never |
| Example 6-6 | | | | | 40 min | 8/10 | almost |
| Example 6-7 | 50° C. | 56 kPa | | 21 kppm | 20 min | 0/10 | never |
| Example 6-8 | | | | | 30 min | 9/10 | almost |
| Example 6-9 | | | | | 40 min | 10/10 | perfect |
| Example 7-1 | 50° C. | 56 kPa | 25% RH | 15 kppm | 10 min | 0/10 | never |
| Example 7-2 | | | | | 20 min | 0/10 | never |
| Example 7-3 | | | | | 30 min | 5/10 | hardly |
| Example 7-4 | | | | | 40 min | 10/10 | perfect |
| Example 7-5 | 50° C. | 56 kPa | | 18 kppm | 10 min | 10/10 | never |
| Example 7-6 | | | | | 20 min | 6/10 | almost |
| Example 7-7 | | | | | 30 min | 10/10 | perfect |
| Example 7-8 | | | | | 40 min | 10/10 | perfect |
| Example 7-9 | 50° C. | 56 kPa | | 21 kppm | 10 min | 1/10 | hardly |
| Example 7-10 | | | | | 20 min | 9/10 | almost |

TABLE 4

| | Temperature | Pressure | Relative humidity | NO₂ concentration | Time | Result | |
|---|---|---|---|---|---|---|---|
| Example 8-1 | 50° C. | 56 kPa | 25% RH | 18 kppm | 10 min | 0/10 | never |
| Example 8-2 | | | | | 20 min | 0/10 | never |
| Example 8-3 | | | | | 30 min | 0/10 | never |
| Example 8-4 | | | | | 40 min | 0/10 | never |
| Example 8-5 | | | | | 50 min | 0/10 | never |
| Example 8-6 | | | | | 60 min | 0/10 | never |
| Example 8-7 | | | | | 70 min | 5/10 | hardly |
| Example 8-8 | | | | 21 kppm | 30 min | 0/10 | never |
| Example 8-9 | | | | | 40 min | 0/10 | never |
| Example 8-10 | | | | | 50 min | 1/10 | hardly |
| Example 8-11 | | | | | 60 min | 8/10 | almost |
| Example 8-12 | | | | | 70 min | 10/10 | perfect |
| Example 9-1 | 50° C. | 56 kPa | 40% RH | 18 kppm | 40 min | 0/10 | never |
| Example 9-2 | | | | | 50 min | 0/10 | never |
| Example 9-3 | | | | | 60 min | 0/10 | never |
| Example 9-4 | | | | | 70 min | 5/10 | hardly |
| Example 9-5 | | | | 21 kppm | 20 min | 0/10 | never |
| Example 9-6 | | | | | 30 min | 0/10 | never |
| Example 9-7 | | | | | 40 min | 0/10 | never |
| Example 9-8 | | | | | 50 min | 0/10 | never |
| Example 9-9 | | | | | 60 min | 1/10 | hardly |
| Example 9-10 | | | | | 70 min | 9/10 | almost |

As shown in Table 3 and 4, it was found that the sterilization characteristics are higher with higher NO₂ concentration, and the sterilization characteristics are higher with longer duration. As shown in Table 4, it was found that sterilization can be performed even if an item is enclosed in a pouch from Examples 8-7, 8-12, 9-4, and 9-10.

Example 10-1

Figure 6:
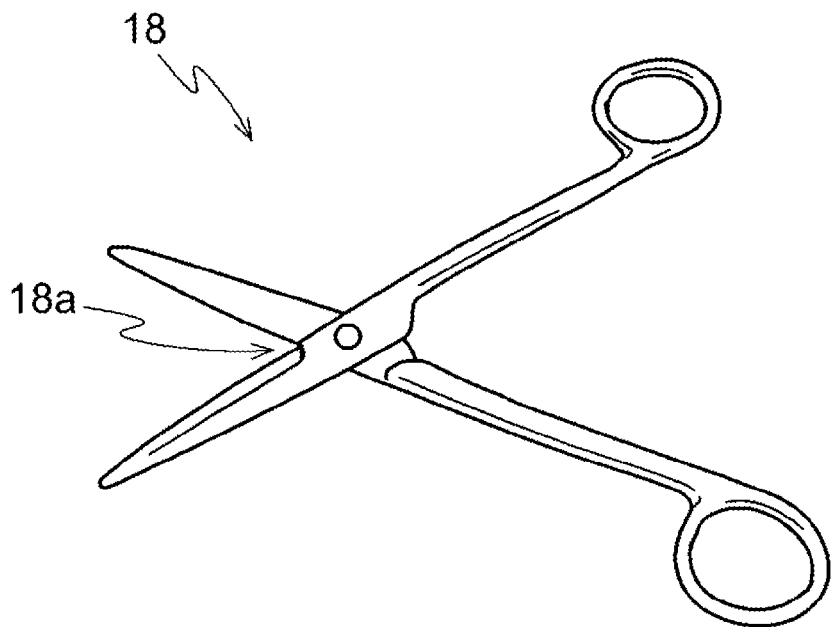
FIG. 6 is a drawing of scissors used in Example 10-1 of the present invention.

A solution (purified water) containing over a million germs (*Geobacillus stearothermophilus*) was applied to a crossover portion 18a of a pair of scissors 18 shown in FIG. 6 and dried. Subsequently, sterilization was performed for 120 minutes for each of three (a prepared NO₂ gas cylinder with a high concentration NO₂ gas (21 kppm concentration) was used, high concentration NO₂ of 20 mg/L) by enclosing it in a polyethylene pouch. Other than those, sterilization was performed in the same manner as in Example 5-1. Germs attaching to the sterilized item were incubated to determine whether sterilization was performed.

0 out of 3 was sterilized as a result.

Example 10-2

Other than NO₂ was filled in the sterilizing chamber to obtain a concentration of 28.8 mg/L by using a prepared NO₂ gas cylinder with a high concentration NO₂ gas (30 kppm concentration), and the duration of sterilization was set to be 240 minutes, sterilization was performed in the same manner as in Example 10-1.

2 out of 3 were sterilized as a result.

Example 10-3

Other than NO₂ was filled in the sterilizing chamber to obtain a concentration of 28.8 mg/L by using a prepared NO₂ gas cylinder with a high concentration NO₂ gas (30 kppm concentration), and the duration of sterilization was set to be 480 minutes, sterilization was performed in the same manner as in Example 10-1.

All 3 were sterilized as a result.

Example 11-1

Figure 7:
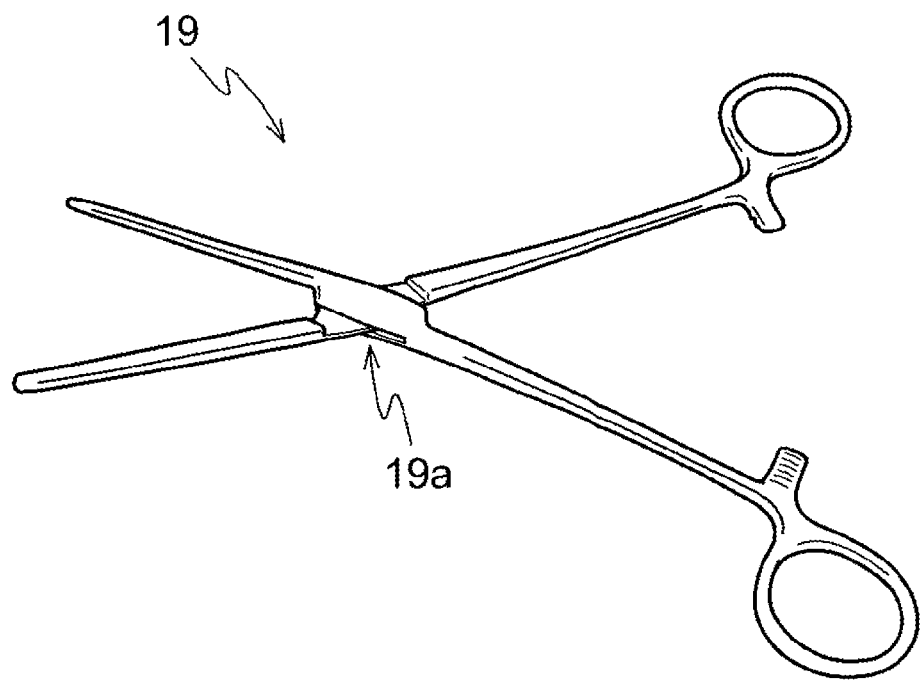
FIG. 7 is a drawing of forceps used in Example 11-1 of the present invention.

A solution (purified water) containing over a million germs (*Geobacillus stearothermophilus*) was applied to a crossover portion 19a of forceps 19 made of stainless steel shown in FIG. 7 and dried. Subsequently, each was enclosed in a polyethylene pouch, and sterilization was performed for 120 minutes for each of three (a prepared NO₂ gas cylinder with a high concentration NO₂ gas (21 kppm concentration) was used, high concentration NO₂ of 20 mg/L) by enclosing it in. Other than those, sterilization was performed in the same manner as in Example 5-1. Germs attaching to the sterilized item were incubated to determine whether sterilization was performed.

0 out of 3 was sterilized as a result.

Example 11-2

Other than NO₂ was filled in the sterilizing chamber to obtain a concentration of 28.8 mg/L by using a prepared NO₂ gas cylinder with a high concentration NO₂ gas (30 kppm concentration), sterilization was performed in the same manner as in Example 11-1.

0 out of 3 was sterilized as a result.

Example 11-3

Other than NO₂ was filled in the sterilizing chamber to obtain a concentration of 28.8 mg/L by using a prepared NO₂ gas cylinder with a high concentration NO₂ gas (30 kppm concentration), sterilization was performed in the same manner as in Example 11-1.

All 3 were sterilized as a result.

Example 12-1

Figure 8:
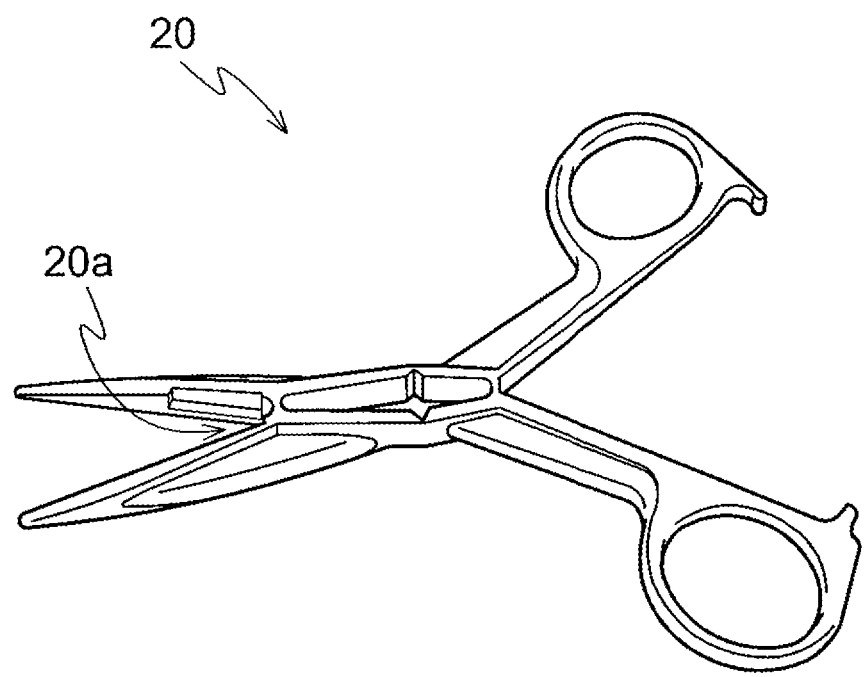
FIG. 8 is a drawing of forceps used in Example 12-1 of the present invention.

A solution (purified water) containing over a million germs (*Geobacillus stearothermophilus*) was applied to a crossover portion 20a of forceps 20 made of plastic shown in FIG. 8 and dried. Subsequently, each was enclosed in a polyethylene pouch, and sterilization was performed for 120 minutes for each of three (a prepared NO₂ gas cylinder with a high concentration NO₂ gas (21 kppm concentration) was used, high concentration NO₂ of 20 mg/L) by enclosing it in. Other than those, sterilization was performed in the same manner as in Example 5-1. Germs attaching to the sterilized item were incubated to determine whether sterilization was performed.

1 out of 3 was sterilized as a result.

Example 12-2

Other than $NO_2$ was filled in the sterilizing chamber to obtain a concentration of 28.8 mg/L by using a prepared $NO_2$ gas cylinder with a high concentration $NO_2$ gas (30 kppm concentration), sterilization was performed in the same manner as in Example 12-1.

1 out of 3 was sterilized as a result.

Example 12-3

Other than $NO_2$ was filled in the sterilizing chamber to obtain a concentration of 28.8 mg/L by using a prepared $NO_2$ gas cylinder with a high concentration $NO_2$ gas (30 kppm concentration), sterilization was performed in the same manner as in Example 12-1.

All 3 were sterilized as a result.
(Effect of sterilization based on the order of humidification and gas filling)

Example 13-1

(Preparation of High Concentration $No_2$ Gas in Chamber)

The high concentration $NO_2$ gas was prepared by the $NO_2$ gas supply system. The air (dew point: −60° C.) was used as an ingredient, and plasma lightning duration in the plasma generator was 25 minutes. The generated high concentration $NO_2$ gas was 40 kppm, and it was stored in the chamber. The pressure at this time, in terms of the differential pressure from the atmospheric pressure (101 kPa (absolute pressure)), was −5 kPa (relative pressure).
(Sterilizing Step)

Figure 9:
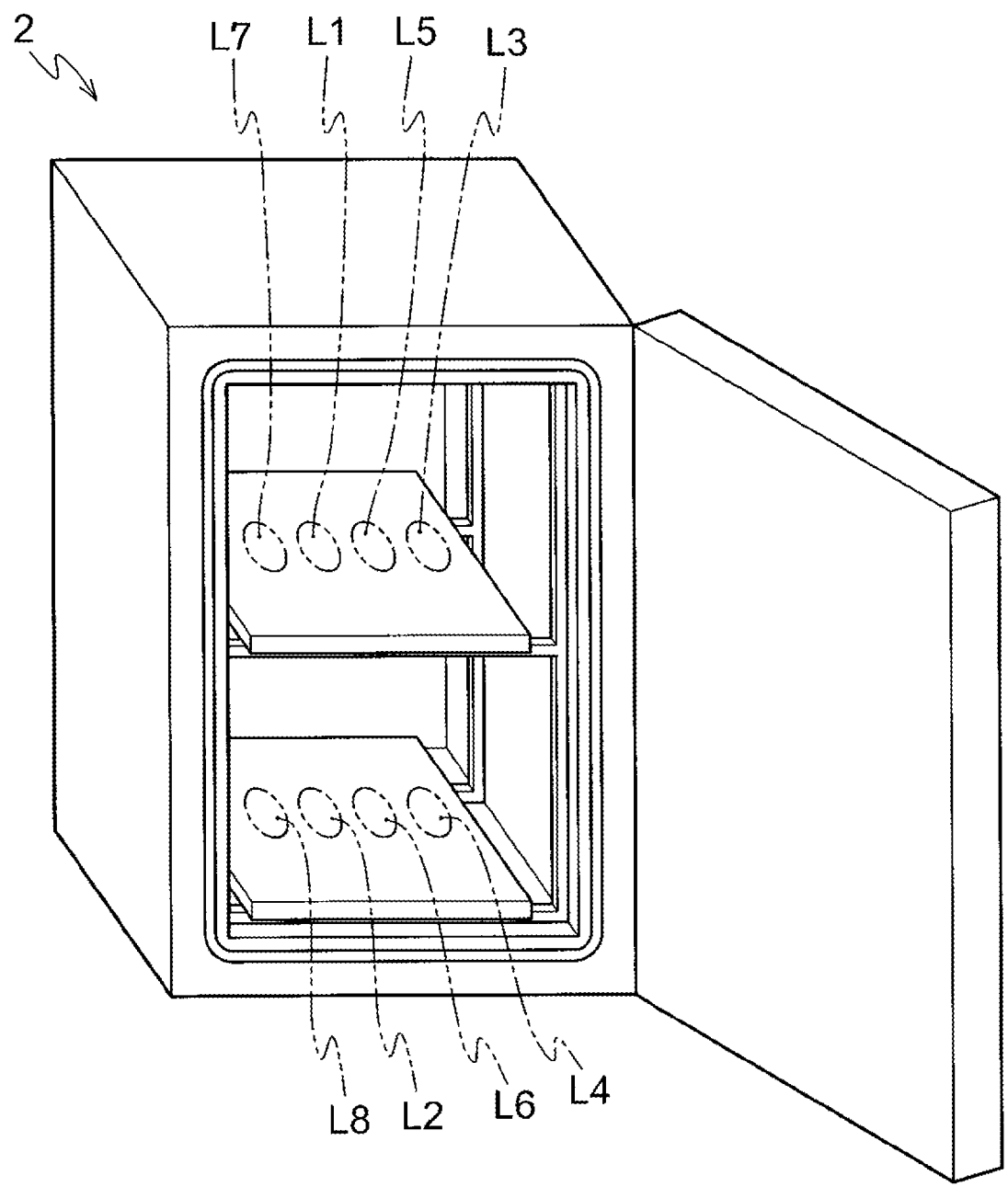
FIG. 9 is an explanatory view illustrating a sterilizing chamber used in Example 13-1 of the present invention.

An SCBI including a glass fiber patch (10 mm diameter, 1 mm thickness) planted with over a million germs (*Geobacillus stearothermophilus*) was placed in the positions of reference numerals L1 and L2 in the sterilizing chamber shown in FIG. 9, an SCBI doubly enclosed in polyethylene nonwoven pouches was placed in the positions of reference numerals L3 and L4, an SCBI placed in a polytetrafluoroethylene (hereinafter, simply referred to as "PTFE") holder disposed in a case in which two tubes (4 mm diameter and 1000 mm length, made of tetrafluoroethylene-hexafluoropropylene copolymer (hereinafter, simply referred to as "FEP")) were connected was placed in the positions L5 and L6, and an SCBI placed in a PTFE holder disposed in a case in which two tubes (1 mm diameter and 500 mm length, made of PTFE) were connected was in the positions L7 and L8. The inside of the chamber was vacuumed by discharging the inside air, and the temperature was set to be 50° C. The humidity was set to be from 25 to 30% RH by filling 3.0 mL of water. The first high concentration $NO_2$ was filled to obtain a concentration of 25 mg/L, and sterilization was performed for 25 minutes. Subsequently, the second high concentration $NO_2$ was filled to obtain a concentration of 50 mg/L, and sterilization was performed for 60 minutes. After sterilization, the high concentration $NO_2$ gas in the sterilizing chamber was discharged, and the sterilized item was taken out.

The experiments were performed twice. The number of sterilized SCBI was counted. The result is shown in FIG. 5.

Example 13-2

After vacuuming the inside of the sterilizing chamber, 1.5 mL of water was filled, the first high concentration $NO_2$ was filled to obtain a concentration of 25 mg/L, and sterilization was performed for 25 minutes. Subsequently, 1.5 mL of water was filled, the second high concentration $NO_2$ was filled to obtain a concentration of 50 mg/L, and sterilization was performed for 60 minutes. Other than those, sterilization was performed in the same manner as in Example 13-1. The result is shown in FIG. 5.

Example 13-3

After vacuuming the inside of the sterilizing chamber, the first high concentration $NO_2$ was filled to obtain a concentration of 25 mg/L, 1.5 mL of water was filled, and sterilization was performed for 25 minutes. Subsequently, the second high concentration $NO_2$ was filled to obtain a concentration of 50 mg/L, 1.5 mL of water was filled, and sterilization was performed for 60 minutes. Other than those, sterilization was performed in the same manner as in Example 13-1. The result is shown in FIG. 5.

Example 13-4

After vacuuming the inside of the sterilizing chamber, the first high concentration $NO_2$ was filled to obtain a concentration of 25 mg/L, and sterilization was performed for 25 minutes. Subsequently, the second high concentration $NO_2$ was filled to obtain a concentration of 50 mg/L, 3 mL of water was filled, and sterilization was performed for 60 minutes. Other than those, sterilization was performed in the same manner as in Example 13-1. The result is shown in FIG. 5.

TABLE 5

| | Temperature | Procedure | Location of sample | | Result |
|---|---|---|---|---|---|
| Example 13-1 | 50° C. | (i) 3.0 mL of water<br>(ii) high conc. $NO_2$<br>(iii) high conc. $NO_2$ | L1<br>L2<br>L3<br>L4<br>L5<br>L6<br>L7<br>L8 | 2/2<br>2/2<br>1/2<br>0/2<br>2/2<br>2/2<br>2/2<br>0/2 | perfect<br>perfect<br>almost<br>never<br>perfect<br>perfect<br>perfect<br>never |
| Example 13-2 | 50° C. | (i) 1.5 mL of water<br>(ii) high conc. $NO_2$<br>(iii) 1.5 mL of water<br>(iv) high conc. $NO_2$ | L1<br>L2<br>L3<br>L4<br>L5<br>L6<br>L7<br>L8 | 2/2<br>2/2<br>2/2<br>2/2<br>0/2<br>0/2<br>0/2<br>0/2 | perfect<br>perfect<br>perfect<br>perfect<br>never<br>never<br>never<br>never |
| Example 13-3 | 50° C. | (i) high conc. $NO_2$<br>(ii) 1.5 mL of water<br>(iii) high conc. $NO_2$<br>(iv) 1.5 mL of water | L1<br>L2<br>L3<br>L4<br>L5<br>L6<br>L7<br>L8 | 2/2<br>2/2<br>1/2<br>1/2<br>0/2<br>0/2<br>0/2<br>0/2 | perfect<br>perfect<br>almost<br>almost<br>never<br>never<br>never<br>never |
| Example 13-4 | 50° C. | (i) high conc. $NO_2$<br>(ii) high conc. $NO_2$<br>(iii) 3.0 mL of water | L1<br>L2<br>L3<br>L4<br>L5<br>L6<br>L7<br>L8 | 0/2<br>0/2<br>0/2<br>0/2<br>0/2<br>0/2<br>0/2<br>0/2 | never<br>never<br>never<br>never<br>never<br>never<br>never<br>never |

As shown in Table 5, the effect of sterilization was high in Examples 13-1 and 13-2 in which water was filled first, and it was found that the effect is obtained even if the high concentration $NO_2$ gas and water are filled in a plurality of times.

Industrial Applicability

According to the sterilization method of the present invention, an excellent effect can be achieved in which a sterilization effect with the increased reliability can be secured even for items to be sterilized having a difficulty in sterilizing due to a factor of such as having a complex form like a narrow opening.

Explanation of Symbols 1 item to be sterilized
2 sterilizing chamber
3 opening
4 shielding door
5 gas supply opening
6 sealing material
7 sterilizing apparatus
8 gas supply system
9 exhausting apparatus
10 humidifying apparatus
11 temperature controlling apparatus
12 circulating means
13 circulating apparatus
14 chamber
15 flow resistive portion
16 plasma generator
17 circulating path
18 scissors
19, 20 forceps
A air inlet portion
C1, C2 tube
D gas drying means
G glass fiber patch
I SCBI
L1, L2, L3, L4, L5, L6, L7, L8 position in which item to be sterilized is disposed
P pump
V1, V2, V3 control valve

What is claimed is:

1. A sterilization method comprising:
   providing a humidifying apparatus for humidifying in a sterilizing chamber and an exhausting apparatus connected to said sterilizing chamber;
   humidifying an inside of said sterilizing chamber containing an item to be sterilized; and
   filling a high concentration $NO_2$ gas from a sub-chamber having a smaller internal volume than that of said sterilizing chamber to obtain a $NO_2$ concentration from 9 to 100 mg/L in the sterilizing chamber,
   wherein said high concentration $NO_2$ gas is filled in said sterilizing chamber after humidifying with said humidifying apparatus, and said humidifying is performed in said sterilizing chamber after a pressure of an inside of said sterilizing chamber is decreased to less than 56 KPa absolute,
   wherein the filling of said high concentration $NO_2$ gas is a step-by-step process comprising filling a part of said high concentration $NO_2$ gas and then further introducing a remaining part of said high concentration $NO_2$ gas one or more times to increase the number of $NO_2$ molecules and an internal pressure in said sterilizing chamber which contains the filled part of said high concentration $NO_2$ gas, and
   wherein an ambient temperature inside of said sterilizing chamber filled with said high concentration $NO_2$ gas is maintained from 10 to 60° C.

2. The sterilization method according to claim 1, wherein said inside of said sterilizing chamber is humidified to obtain a relative humidity from 10 to 90% R.H.

3. The sterilization method according to claim 1, wherein said humidifying apparatus is configured to include an evaporation portion communicating with said sterilizing chamber, and a heater for heating said evaporation portion.

4. The sterilization method according to claim 1, wherein said humidifying is performed or said high concentration $NO_2$ gas is filled in said sterilizing chamber after a pressure of an inside of said sterilizing chamber is decreased to 0.01 KPa to 1 KPa absolute.

5. The sterilization method according to claim 1, wherein said high concentration $NO_2$ gas is generated by displacing a gas mixture including nitrogen and oxygen into a plasma state with a plasma generator.

6. The sterilization method according to claim 1, wherein a pressure difference between an outside atmospheric pressure and a pressure in said sterilizing chamber at a time of completing a filling of said high concentration $NO_2$ is from −1 KPa to −95 KPa absolute.

7. The sterilization method according to claim 1, wherein an item to be sterilized having a narrow opening with an internal diameter of 1 to 4mm is contained in said sterilizing chamber between 10 and 480 minutes, and wherein said sterilizing chamber is humidified to reach a relative humidity from 10 to 90% R.H., and is filled with said high concentration $NO_2$ gas to obtain an $NO_2$ concentration from 9 to 100 mg/L in said sterilizing chamber.

8. The sterilization method according to claim 1, wherein an item to be sterilized having crossover opposing surfaces is contained in said sterilizing chamber between 10 and 480 minutes, and wherein said sterilizing chamber is humidified to reach a relative humidity from 10 to 90% R.H., and is filled with said high concentration $NO_2$ gas to obtain an $NO_2$ concentration from 9 to 100 mg/L in said sterilizing chamber.

* * * * *